United States Patent [19]

Rubin

[11] Patent Number: 5,639,737

[45] Date of Patent: Jun. 17, 1997

[54] METHOD AND COMPOSITIONS FOR TREATING MALIGNANT TUMORS AND INHIBITING GROWTH AND METASTASES OF MALIGNANT TUMORS

[75] Inventor: David Rubin, San Diego, Calif.

[73] Assignee: Co Enzyme Technology Ltd., San Diego, Calif.

[21] Appl. No.: 360,352

[22] Filed: Dec. 21, 1994

Related U.S. Application Data

[63] Continuation-in-part of Ser. No. 138,195, Oct. 20, 1993, Pat. No. 5,476,842, which is a continuation-in-part of Ser. No. 57,666, Pat. No. 5,340,803, filed as PCT/US92/09743 Nov. 4, 1992 which is a continuation-in-part of Ser. No. 787,347, Nov. 4, 1991, abandoned.

[51] Int. Cl.$^6$ ..................................................... A61K 31/70
[52] U.S. Cl. .............................. 514/53; 514/23; 536/4.1; 536/123.13
[58] Field of Search ........................... 530/396, 402, 530/408, 409; 514/2, 23, 25; 536/4.1, 123.13

[56] References Cited

U.S. PATENT DOCUMENTS

| | | | |
|---|---|---|---|
| 4,337,760 | 7/1982 | Rubin | 128/1 R |
| 4,424,348 | 1/1984 | Rubin | 536/179 |
| 4,481,195 | 11/1984 | Rubin | 424/137 |
| 4,584,368 | 4/1986 | Rubin | 536/4.1 |
| 4,812,590 | 3/1989 | Saari | 860/137 |
| 4,946,830 | 8/1990 | Pulverer et al. | 514/23 |
| 5,225,542 | 7/1993 | Cramer et al. | 530/396 |
| 5,239,062 | 8/1993 | Blattler et al. | 530/396 |
| 5,340,803 | 8/1994 | Rubin | 514/25 |
| 5,395,924 | 3/1995 | Blattler et al. | 530/396 |

FOREIGN PATENT DOCUMENTS 9204048  3/1992  WIPO.

OTHER PUBLICATIONS

Smit et al., *Melonoma Res.*, vol. 2(5–6), pp. 295–304, (1992).

Naish-Byfield et al., Melanoma Res., vol. 1(4), pp. 273–287, (1991).

Assaf et al., Planta Med., vol. 53(4), pp. 343–345, (1987).

Firon et al., Infect. Immun., vol. 55(2), pp. 472–476, (1987).

Lotan et al. Carbohydrate Research, vol. 213, pp. 47–57, (1991).

Nakamura et al. Medical Journal of Kiniki University, vol. 19(4), pp. 537–551, (1994).

Platt et al. J. Natl. Cancer Inst., vol. 84(6), pp. 438–442, (1992).

Database Chemabs, Chemical Abstracts Service, Columbus, Ohio, Naito, Albert T., "Substances Penetrating the Blood–Brain Barrier," JP A 05 339 148, AN=120:208571.

Database Medline, U.S. National Library of Medicine, Bethesda, Maryland AN=68362667 & Archiv Furgeschwulstforschung, vol. 29, No. 3, 1967, pp. 226–273, Tanneberger et al., "On the Value of Chloroquine in the Treatment of Malignant Tumor Diseases".

Avraham et al., "Lectin–Like Activities Associated with Human and Murine Neoplastic Cells," Cancer Research, vol. 41, Sep. 1981 MD US, pp. 3642–3647.

Kaneko et al. Chem. Pharm Bull. vol. 25 (9), pp. 2458–2460.

Baba et al. Gann vol. 69, pp. 283,284, (1978).

Primary Examiner—John Kight
Assistant Examiner—Howard C. Lee
Attorney, Agent, or Firm—Browdy and Neimark

[57] ABSTRACT

Growth or metastasization of malignant tumors can be inhibited by administering to a patient in need thereof sufficient lactose to block crucial lectins on the affected organ so that the tumor cells cannot anchor to other locations in the body. Lactose can be administered alone, or in combination with conjugates of cytotoxic drugs. Preferably, lactose is conjugated to a cytotoxic substance so that the primary tumor is treated concurrently with prevention of metastasis. Additionally, by conjugating a cytotoxic drug to lactose, the cytotoxic drug is maintained in close proximity to the tumor because of the receptors on the tumor which bind the lactose (and therefore the cytotoxic agent bound thereto) to the tumor cells. By using a conjugate of lactose with a cytotoxic agent, one dose is generally sufficient to destroy the receptor sites on the tumor and prevent metastasis of the tumor while treating the tumor.

23 Claims, No Drawings

METHOD AND COMPOSITIONS FOR TREATING MALIGNANT TUMORS AND INHIBITING GROWTH AND METASTASES OF MALIGNANT TUMORS

This is a continuation-in-part of Ser. No. 08/138,195, filed Oct. 20, 1993, now U.S. Pat. No. 5,476,842, which is a continuation-in-part of Ser. No. 08/057,666, filed May 5, 1993, now U.S. Pat. No. 5,340,803, which is a continuation-in-part of PCT/US92/09743, filed Nov. 4, 1992, which is a continuation-in-part of Ser. No. 07/787,347, filed Nov. 4, 1991, now abandoned, the entire contents of all of which are hereby incorporated by reference.

FIELD OF THE INVENTION

The present invention is directed to methods and compositions for treating malignant tumors and other metastatic diseases and for inhibiting the metastases of malignant tumors.

BACKGROUND OF THE INVENTION

The formation of metastases of malignant tumors, which initiate from a primary tumor at more or less remote locations of the body, is one of the most serious problems of tumor therapy, since most of the fatal conditions are caused by such metastases. In recent years there has been considerable success in treating primary tumors by surgery, radiation therapy and chemotherapy. In contrast thereto, the treatment of metastases is extremely difficult and only rarely successful. The risk of metastasis formation is particularly high during the treatment of primary tumors, so that there is an urgent need for preventing the formation of metastases, particularly in this phase.

Exposed cell surface carbohydrate-containing macromolecules have been implicated in growth, morphogenesis, differentiation, recognition, intercellular interactions, and adhesion of tumor cells. Certain surface changes associated with transformation and neoplasia may lead to alterations of the above fundamental processes. Therefore, it is important to study the tumor cell surface characteristics in order to understand factors which influence the expression of the malignant phenotype. The surface properties of tumor cells play a major role in tumor growth at the primary site, invasion into surrounding host tissue, dissemination, embolization, and implantation at distant secondary sites to form metastases. Specifically, in an experimental model of metastasis, that of B16 melanoma (Fidler, Nat. New. Biol. 242: 148–149, 1978; Nicolson et al., Cancer Res. 38: 4105–4111, 1978), it has been shown that tumor cell clumps produce more lung metastases after intravenous injection than do single cells (Fidler, Eur. J. cancer, 9: 223–227, 1973). Further in vitro studies using B16 melanoma variants exhibiting different metastatic potential demonstrated a correlation between the tendency of cells to undergo both homotypic and heterotypic aggregation in vitro, and their metastatic potential in vivo (Fidler et al., Cancer Res, 37: 3945–3956, 1977; Gasic et al., Int. J. Cancer 11: 704–716, 1973; Nicolson et al., Nature (Lond.) 255: 230–232, 1975; Raz et al., Nature (Lond.) 284: 363–364, 1980; Winkelhake et al., J. Nat. Cancer Inst. 56: 285–291, 1976). The homotypic aggregation of B16 melanoma cells depended on the presence of fetal bovine serum. One possible explanation for this requirement could be that a serum glycoprotein(s) mediated intercellular adhesion similar to the action of cell—cell adhesion molecules in other vertebrate systems.

Thorough investigations of metastasis formation, i.e., of organ-specific and non-organ-specific metastases, have resulted in the finding that organ cell lectins are responsible for the formation of metastases. Lectins are highly specific sugar-binding molecules which were first found only in plants, but later on in nearly all other living creatures, including vertebrates. The lectins apparently mainly serve to recognize sugar structures on cell surfaces or in soluble glycoconjugates.

It has further been found that organ cell lectins are responsible for the specific organotropic metastasization. In the course of further intensive investigations it has been found that the formation of metastases of malignant tumors can even be prevented by saturating the lectins of these organ cells with the monosaccharides which are specific for the lectins, and/or with the glycoconjugates containing the monosaccharides in the terminal position.

Monoclonal antibodies have been considered as delivery agents for cytotoxic drugs to treat cancers and to inhibit metastasis of existing cancers. However, there is such a high density of receptors on the surface of cancer cells, and the monoclonal antibodies are such large compounds, that it is impossible to provide sufficient monoclonal antibodies at the cell surface to effectively destroy the cancer cells. The large monoclonal antibodies, in other words, are so large that only a very few can be present at the surface of a cell at any one time.

It is increasingly believed that there is a genetic predisposition to some types of cancer, including some types of colon cancer and some types of breast cancer. Additionally, there are some types of cancers which may be aggravated or caused by a person's behavior or diet, such as smoking causing lung cancer, or a high fat, low fiber diet contributing to the onset of colon cancer. It would be particularly useful for those persons who are at high risk for cancer to be able to act to prevent development of cancer.

Pulverer et al., in U.S. Pat. No. 4,946,830, disclose the use of $\beta$-D-galactose and/or glycoconjugates containing terminal $\beta$-D-galactose, for inhibiting metastasis of malignant tumors. Other monosaccharides are mannose and glycoconjugates containing a terminally or centrally located mannose as well as L-fucose, N-acetylglucosamine, N-acetylgalactosamine, N-acylneuraminic acids, and derivatives containing neuraminic acid. While the saccharide may be bonded to a carrier, the carrier molecule itself should not be cytotoxically active against tumor cells.

Raz et al., Cancer Research 41: 3642–3647, 1981, disclose that tumor cells include a carbohydrate-binding component(s), which binding was most strongly inhibited by lactose.

Raz et al., ibid., disclose that endogenous lectins on a number of tumor cells exhibited a potent capacity to agglutinate trypsin-treated glutaraldehyde fixed rabbit erythrocytes. This activity was inhibited by millimolar concentrations of lactose, whereas D-galactose, D-galactosamine, and N-acetyl-D-galactosamine were much less potent inhibitors. D-mannose, L-fucose and N-acetyl-O-glucosamine failed to inhibit hemagglutination even at 0.2M.

There have been many reports in the literature relating to the general concept of providing direct transport of an agent which is toxic to tumor cells directly to tumors having $\beta$-glucuronidase activity by conjugating the agent with glucuronic acid. Among such reports are Von Ardenne, M. et al., *Agressologie,* 1976, 176(5): 261–264; East German Patent No. 122,386; German Offenlegungsschrift 22 12 014; Sweeney et al., *Cancer Research* 31: 477–478, 1971; Baba et al., *Gann,* 69: 283–284; and Ball, *Biochem. Pharm.* 23: 3171–3177 (1974).

Von Ardenne et al. suggest many types of aglycones which may be conjugated to glucuronic acid and will be active at the tumor site. These include, broadly, alkylating groups, antimetabolites, cytotoxins, membrane-active (lytic) groups, glycolysis stimulators, respiration inhibitors, inorganic and organic acids and cell cycle stoppers. The East German patent cited above also suggests many such combinations, including 5-fluorouracil-glucuronide, aniline mustard-glucuronide, and many others. The Offenlegungsschrift also mentions a large number of glucuronides. Sweeney et al. disclose the anti-tumor activity of mycophenolic acid-β-glucuronides. Bab et al. note the anti-tumor activity of 5-fluorouracil-o-β-D-glucuronide, and Ball discloses the anti-tumor activity of p-hydroxyaniline mustard glucuronide.

Kneen in European Patent Application 054,924, discloses phenyl ether compounds which can be used to make tumors more sensitive to radiotherapy.

Rubin, in U.S. Pat. Nos. 4,337,760 and 4,481,195, discloses methods for treating tumors having high β-glucuronidase activity with glucuronides with aglycones toxic to the tumor cells with great safety toward the rest of the body by first administering an alkalinizing agent in an amount sufficient to maintain the pH level of non-tumor tissues at approximately 7.5 during the glucuronide treatment to inactivate β-glucuronidase activity in the rest of the body. Thus, the toxic agent is directed only at the cancer cells, as opposed to all of the healthy cells of the body, since the aglycone is only released at the site of the cancer. Tumors having high glucuronidase activity can be identified by assaying tumor cells obtained in a biopsy for β-glucuronidase activity, or by administering a glucuronide whose aglycone has been labelled with a radioactive isotope. If, upon a full body scan, it is found that the radioisotope has accumulated at any specific areas of the body, this will indicate not only the location of the tumor, but the fact that the tumor has sufficient β-glucuronidase activity to deconjugate the glucuronide.

The rationale for the use of 4-hydroxyanisole in the treatment of melanoma is based upon the premise that the only cells in vertebrates that contain tyrosinase are the melanocytes. 4-Hydroxyanisole inhibits DNA synthesis, but by itself shows little toxicity. However, 4-hydroxyanisole is oxidized by tyrosinase to form highly cytotoxic products, and consequently 4-hydroxyanisole is preferentially toxic to those melanoma cells that contain the enzyme tyrosinase [Riley, *Philos. Trans. R. Soc. (Biol.)* 311: 679, 1985]. Morgan et al., in *Clinical Oncology* 7: 227–231, 1981, also note that 4-hydroxyanisole, which is oxidized by tyrosinase, gives rise to cytotoxic oxidation products. The specific melanocytotoxic action of this agent is of particular interest because of its use in treatment of malignant melanoma. It was found that localized malignant melanomas treated by intra-arterial infusion of 4-hydroxyanisole underwent regression, although intravenous administration of the drug was not therapeutically effective. The need to use the intra-arterial route of administration imposes certain limits on the use of 4-hydroxyanisole, since it is not always possible to perfuse the site occupied by a tumor. However, it is believed that, as an adjunct to the conventional treatment of primary melanoma in accessible sites, 4-hydroxyanisole infusion will reduce the dissemination of metastases.

Kanclerz et al., in *Br. J. Cancer* 54: 693–698, 1986, reported that animal studies on experimental melanomas have seen variable results with respect to the therapeutic efficacy of phenolic depigmentation agents. The most active melanocytotoxic agent was found to be an analog of tyrosine, 4-hydroxyanisole. However, evidence for an anti-tumor effect of 4-hydroxyanisole on melanoma in vivo was found to be variable and not conclusive.

Unfortunately, intra-arterial infusion of 4-hydroxyanisole has serious clinical drawbacks, including difficulties in placing and maintaining the patency of intra-arterial catheters. Clogging and/or clotting frequently occur, and, further more, 4-hyroxyanisole has a short half-life in blood, only about nine minutes, after intra-arterial injection.

Saari, in U.S. Pat. No. 4,812,590, discloses that certain carbamates of 4-hydroxyanisole are suitable substitutes for 4-hydroxyanisole in the treatment of melanoma. These carbamates can be delivered by, for example, intravenous injection, and provide increased levels of 4-hydroxyanisole at the tumor site. The delivery of 4-hydroxyanisole is more convenient and safer than many other methods of delivering 4-hydroxyanisole, although, because serum tyrosinase levels may be elevated in patients having tumors with high tyrosinase activity, the metabolic products of 4-hydroxyanisole may be present in locations other than the tumor site.

Pavel et al., *Pigment Cells Research* 2: 241–246, 1989, reported an investigation of the human metabolism of 4-hydroxyanisole using urine samples from melanoma patients treated with 4-hydroxyanisole. The most important metabolite of 4-hydroxyanisole was found to be 3,4-dihydroxyanisole, although other metabolic products included 3-hydroxy-4-methoxyanisole and 4-hydroxy-3-methoxyanisole, as well as quinone. These compounds were excreted predominantly as sulfates and glucuronides. Unfortunately, when tyrosinase oxidizes 4-hydroxyanisole in the body, the product, 4-methoxybenzoquinone, is extremely toxic. Because the 4-hydroxyanisole is not confined to the tumor site, and because the serum level of tyrosinase of patients suffering from tyrosinase-active tumors tends to be elevated, there is always the danger in administering 4-hydroxyanisole to such patients whereby an excess of metabolic products of 4-hydroxyanisole will be present in the blood, and thus exert a cytotoxic effect on cells other than tumor cells.

Chen et al. discovered that serum tyrosinase activity in many persons with metastatic diseases was significantly higher than activity in normal persons. Although the highest serum tyrosinase activity was observed in melanoma and breast carcinoma, there is measurable tyrosinase activity in a variety of other metastatic diseases, including lung carcinoma, colon carcinoma, testicular carcinoma, hepatic carcinoma, pancreatic carcinoma, ovarian carcinoma, leukemia, bronchogenic carcinoma, prostate carcinoma, Hodgkin's disease, and rectal carcinoma, the tyrosinase activity of the foregoing diseases listed in decreasing order.

In addition, serum melanin bands were demonstrated by polyacrylamide disc gel electrophoresis of serum tyrosinase followed by incubation of the gel with L-dopa at room temperature overnight to form melanin bands. The following types of metastatic disease demonstrated serum melanin bands with this technique: mouth carcinoma, multiple myeloma, carcinoma of the stomach, carcinoma of the larynx, carcinoma of the cervix, carcinoma of the tonsil, lymphoma, lymphosarcoma, thyroid carcinoma, carcinoma of cecum, endometrial carcinoma, polycytehmia, thymoma, lymphadenopathy, and vertebral carcinoma.

Although the elevation of serum tyrosinase level is explicable in some diseases such as melanoma and breast carcinoma, the high tyrosinase content in melanoma and breast skin increases the tyrosinase circulation level in the blood. Although it has not yet been determined if malignant disease causes a high yield of serum tyrosinase or if a high yield of serum tyrosinase causes malignant disease, it has been postulated that serum immunoglobulins are involved as tyrosinase carriers. Whatever the involvement of tyrosinase in metastatic diseases, there is an elevated level of serum tyrosinase in the case of a great many metastatic diseases.

Passi et al., in *Biochem. J.* 245: 536–542, 1987, compressed the cytotoxicity of a number of phenols in vitro. These researchers found that in vitro, two melanotic human melanoma cell lines, IRE1 and IRE2, and the lymphoma- and leukemia-derived cell lines Raji and K652, exhibited no significant differences in percentage survival among the different cell lines for each drug tested. The major component of toxicity up to 24 hours of di- and tri-phenols was due to toxic oxygen species acting outside the cells, and not to cellular uptake of these phenols per se. It is believed that scavenger enzymes may interfere with the cytotoxic effect of some of these phenols. Additionally, it was noted that the cytotoxic effect of these phenols was not necessarily related to their being substrates for tyrosinase, as the level of toxicity of butylated hydroxyanisole, which is not a substrate of tyrosinase, was significantly higher than that of 4-hydroxyanisole, which is a substrate of tyrosinase.

With respect to dosages of 4-hydroxyanisole to be given, Wallerie et al. report in "Non-Specific Inhibition of In Vitro Growth of Human Melanoma Cells, Fibroblasts and Carcinoma Cells by 4-Hydroxyanisole" in *Hydroxyanisole: Recent Adv. Anti-Melanoma Ther.*, pp. 153–164 (1984) Editor, Patrick A. Riley, that 4-hydroxyanisole was inhibitory to cultures of human melanotic and amelanotic melanoma cell lines, human fibroblasts and a human bladder carcinoma at concentrations of $10^{-3}$M to $10^{-5}$M. This activity was independent of tyrosinase activity, as high tyrosinase activity was only connected with the melanotic cell line, Unfortunately, the therapeutic concentration of 4-hydroxyanisole is difficult to obtain in tissue by intra-arterial infusion of the drug. Furthermore, infusion is given only for one hour twice a day, which is an exposure of the cells that in vitro has no inhibitory effect, even at a high concentration of 4-hydroxyanisole.

It has also been found that a genetic aberration in chromosomes 7 and 13 of certain malignant growths expresses itself in a vast biosynthesis of two specific enzymes: β-glucuronidase and tyrosinase. Among these malignant growths are breast cancer, lung cancer, colon caner, melanoma and gastric cancer.

Para-methoxy-phenyl glucuronide damages cancer cells by excessive production of hydrogen peroxide. Hydrogen peroxide oxidizes many amino acid side chains, such as methionine, by transferring one of the oxygen atoms from the hydrogen peroxide to an acceptor molecule, resulting in damage to the cells. However, cancer cells as well as other living cells contain reduced glutathione (GSH). Glutathione, a tripeptide made up of glutamic acid, cysteine, and glycine, in its reduced state as GSH, can react with hydrogen peroxide to mitigate the oxidative damage to cell membranes, as shown in the following equation:

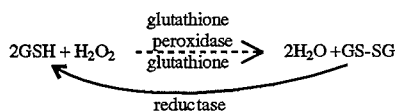

SUMMARY OF THE INVENTION

It is an object of the present invention to overcome the aforementioned deficiencies in the prior art.

It is another object of the present invention to provide a method and composition for treating metastatic cells.

It is another object of the present invention to provide a composition and method for treating metastatic cells without damaging normal cells.

It is another object of the present invention to provide a method and composition for treating malignant tumor cells while simultaneously inhibiting metastasis of the malignant tumor cells.

According to the present invention, lactose is administered to a patient at high risk of cancer or to a patient undergoing treatment for cancer, including surgery, to prevent development or metastasis of cancer. The lactose may be administered by itself or conjugated to a cytotoxic substance so that the primary tumor is treated concurrently with prevention of metastasis. Additionally, by conjugating a cytotoxic drug to lactose, the cytotoxic drug is maintained in close proximity to the tumor because of the receptors on the tumor which bind the lactose (and therefore the cytotoxic agent bound thereto) to the tumor cells. By using a conjugate of lactose with a cytotoxic agent, one dose is generally sufficient to destroy the receptor sites on the tumor and prevent metastasis of the tumor while treating the tumor. Lactose is particularly effective in treating cancer and preventing metastasis thereof because the affinity of lactose for receptors on the surface of cancer cells is more than 100 times that of galactose.

The lactose is administered alone or conjugated to a cytotoxic drug. Because lactose is a relatively small molecule, many molecules of lactose can be present at the surface of a cell, so that many receptor sites are filled by lactose molecules. In one embodiment, at least one cytotoxic phenol which is a substrate for tyrosinase is conjugated to at least one saccharide to provide at least one compound for treating tumors which have both saccharidase activity and tyrosinase activity. The saccharide, upon contact with the saccharidase, is cleaved to produce the tyrosinase substrate cytotoxic phenol at the tumor site, which, upon being acted upon by tyrosinase, then can exert its cytotoxic effect on the tumor cells. In this manner, the truly toxic compound is delivered only to the tumor cells, and there is virtually no contact with the healthy cells, since the cytotoxic phenol is not released at the tumor site until the saccharide compound has been cleaved by the saccharidase at the tumor site. This avoids contact of healthy cells with the cytotoxic phenol, and the reaction products of the cytotoxic phenol and any tyrosinase can be limited to the tumor site. By using a plurality of saccharides, one can obtain a synergistic effect in treating tumors having tyrosinase activity, since the different saccharide molecules act at different sites on the tumor membrane.

A combination of saccharide conjugates can be used in conjunction with lactose or a lactose conjugate; such combination can be chosen for use in treating tumors can be chosen to have the maximum effect for the particular tumor treated. For example, melanomas have both α-D-glucosidase activity as well as β-D-glucuronide activity. Therefore, melanomas are treated with a saccharide conjugate of α-D-glucoside and a tyrosinase substrate as well as a saccharide conjugate of β-glucuronide with a tyrosinase substrate. In order to prevent metastases, one of the saccharides can be lactose, or lactose can be administered in conjunction with the saccharide conjugates. Mammary tumors, on the other hand, have a very high β-galactosidase activity, and these tumors are effectively treated by conjugating β-D-galactoside to a cytotoxic phenolic compound, which can be used in conjunction with a conjugate of a cytotoxic phenolic compound with a β-D-glucuronide. One skilled in the art can readily determine what saccharide enzyme or enzymes activity a particular tumor possesses, and tailor the combination of conjugates for optimum destruction of the tumor.

When the saccharide used to make the conjugate is lactose, the cytotoxic drug is used to destroy the receptor sites on the tumor and the lactose part of the conjugate acts to prevent metastasis of the tumor while the cytotoxic portion treats the tumor.

The cytotoxic phenolic compounds which are substrates for tyrosinase compounds which can be used in the present invention are those which have been found to be toxic to human tumor cells, including tyrosine, 4-hydroxyanisole, butylated hydroxyanisole, L-3,4-dihydroxyphenylalanine, dopamine (3,4-dihydroxyphenethylamine), tertbutylcatechol, hydroquinone, resorcinol, 6-hydroxydopa (3,4,6-trihydroxyphenylalanine), 4-tert-butyl phenol, 4-tert-amyl phenol and 4-benzomethoxy phenol and methyl gallate. These compounds are conjugated to glucuronic acid and/or saccharides by any convenient means to form the compounds of the present invention. Of particular importance when the saccharide is lactose is benzyl alcohol, which is oxidized to benzaldehyde at the site of the cancer, and 7-hydroxy coumarin, which is otherwise too toxic to be administered in sufficient dosage to destroy the cancer cells.

The saccharide other than lactose is any saccharide that can be conjugated to a cytotoxic phenol and which is readily cleaved from the phenol by an enzyme particular to a tumor. Several, nonlimiting, examples of such saccharides include glucose, galactose, fructose, arabinose, mannose, gulose, ribose, xylose, lyxose, erythrose, maltose, cellobiose, sucrose, N-acetyl glucosamine, N-acetyl galactosamine, and rhamnose. As noted above, lactose is preferred.

In addition, the cytotoxic phenolic compounds conjugated to the saccharides can be used in the acetylated form. That is, when the conjugates are prepared by conjugating a phenolic compound with methyl(tri-O-acetyl-α-D-glycosyl bromide)-uronate, a triacetyl methyl ester is formed. This triacetyl methyl ester can be used in the acetylated form. Since these acetyl groups are not easily removed, the compounds are not particularly cytotoxic to normal cells. However, since primitive cells, such as growing cancer cells, can produce many different types of enzymes, including acetylase, these primitive cells can readily remove the acetyl groups on the acetylated conjugates to provide active forms of the compound directly at the site of a growing tumor. Of particular importance are the 3-acetylated conjugates, since the 3-acetylated conjugates are lipid soluble and are retained by the body at the tumor site for a much longer period of time than the unacetylated conjugates. The 3-acetylated conjugates have also been found able to cross the blood-brain barrier. When lactose is the saccharide, the lactose may be heptacetylated.

When the saccharide is lactose, a preferred conjugate is a conjugate of lactose with benzyl alcohol. Lactose may be used in its free form or as a heptacetylated molecule.

Of the compounds of the present invention, one preferred compound is para-methoxy phenyl lactose, or PMP lactose. Because this compound is a lactose conjugate, it possesses a low toxicity. This lactose conjugate is used with the appropriate glycon conjugate of a cytotoxic phenolic compound, such as a conjugate of lactose and 4-hydroxy-anisole, for treating tumors.

Para-methoxy-phenyl lactose has the following formula:

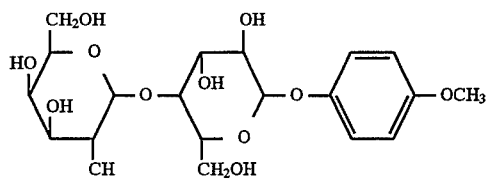

Para methoxy phenyl lactose

Of the glucuronide conjugates of the present invention, the glucuronide of 4-hydroxy-anisole (or PMPG, for para-methoxy-phenyl-glucuronide) is another one preferred compound. Because this compound is a glucuronide, it possesses a low toxicity, as an important mechanism of the liver is to detoxify toxins via conjugation with glucuronic acid. This glucuronide conjugate is used with the appropriate glycon conjugate of a cytotoxic phenolic compound, such as a conjugate of galactose and 4-hydroxy-anisole, for treating tumors.

Para-methoxy-phenyl glucuronide has the following formula:

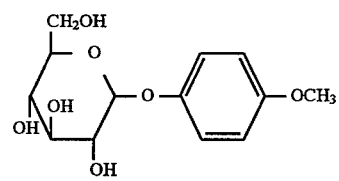

Para methoxy phenyl glucuronide

Other saccharide molecules are conjugated to cytotoxic phenols in a similar manner.

In another embodiment of the present invention, the prodrug to be used with administration of lactose or a lactose conjugate is a combination of equal parts of para-methoxy-phenyl glucuronide and para-methoxy-phenyl-aglycon, both of which are hydrolyzed at the cancer site by β-glucuronidase and β-galactosidase, respectively, to yield 4-hydroxyanisole (para-methoxy phenol). The 4-hydroxy anisole then becomes a substrate for the enzyme tyrosinase, which oxidizes the 4-hydroxy anisole to methoxy ortho benzoquinone. The methoxy ortho benzoquinone is an unstable molecule that spontaneously releases hydrogen peroxide. This released hydrogen peroxide damages the cell membranes. The inhibition of glutathione reductase by a quinone compound further enhances the oxidative damage in the cancerous cells.

In yet another embodiment of the present invention, benzaldehyde is conjugated to lactose. The benzaldehyde at the tumor site crosslinks the receptors, thus destroying the active tumor site and any opportunities the tumor may have to metastasize.

DETAILED DESCRIPTION OF THE INVENTION

Lactose, either alone or conjugated to a cytotoxic drug, is specific for organ cell lectins, and thus can be used either for the prevention of metastases of malignant tumors and/or for treatment of malignant tumors. Since lactose and glycoconjugates containing lactose are well compatible, treatment can be carried out in a simple manner. The active substances may be administered enterally a well as parenterally, and are metabolized from the organism in a known manner. The relatively high serum level of lactose used must be sufficient to block the crucial organ cell lectins as long as there is a danger of an increased metastasization due to treatment of investigation of the primary tumor. Monoclonal antibodies against the organ cell lectins stop the metastasization in a manner similar to lactose and lactose glycoconjugates. The advantage of using lactose or conjugates of lactose is that the lactose and conjugates thereof are much simpler and cheaper to prepare.

One example of metastasization that can be prevented by the present invention is the metatastization of colon carcinoma which tends to form metastases in the liver. This type of metastasis can be prevented by administering an effective amount of lactose or a glycoconjugate containing lactose such as PMPG. The administration of lactose is only necessary for a relatively short period of time before and after treatment of the primary tumor, or shortly before and after diagnostic interventions that might potentially result in metastasization in cases of suspicion of a tumor. However, if there are no observable side effects, the lactose or glycogonjugates thereof may be administered from the time of diagnosis of the tumor until some weeks after therapy has concluded.

A number of methods can be used to manufacture the saccharide conjugates according to the present invention, including those disclosed in Rubin, U.S. Pat. No. 4,481,195 and Rubin, U.S. Pat. No. 4,424,348, the entire contents of both of which are incorporated by reference.

The cytotoxic phenols are conjugated to the saccharide by conjugation of the phenol with methyl (tri-O-acetyl-α-D-aglycon bromide)-uronate, the active form of the saccharide for conjugation, and may be produced in accordance with the teachings of Bollenback et al., *J. Am. Chem. Soc.* 77: 3310, 1955, the entire contents of which are hereby incorporated by reference.

The cytotoxic phenol is introduced to the methyl(tri-O-acetyl-α-D-aglycon bromide) uronate in a solution of phenol catalyzed by a small, catalytic amount of silver oxide. Besides phenol, there may be used as a solvent quinoline, methyl nitrile, or methyl cyanide. Silver carbonate may be used as the catalyst in place of silver oxide.

Another method of condensation is to use sodium or potassium hydroxide as the condensing agent in aqueous acetone solution. A stoichiometric excess of cytotoxic phenol is preferably used. The reaction solution is maintained at room temperature for 24 hours, or until the reaction to form the triacetyl methyl ester is complete.

The triacetyl methyl ester can be used as such or can be converted to the acid form of the conjugate by reaction of the triacetyl methyl ester as obtained above with a ½ molar amount of 0.5N barium hydroxide which is added slowly to this solution to form a white precipitate. Preferably, an excess of barium hydroxide is added until there is no more precipitation.

The addition of 0.5N sulfuric acid, volume to volume, followed by cooling in ice water for 20 minutes, releases the free saccharide.

The mixture is then filtered, and the supernatant is dried in vacuum and crystallized from ether.

The triacetylated form of the saccharide is the preferred form of the compounds to be used in accordance with the present invention. However, the free acid form of the conjugates may also be used when a water-soluble form of the conjugate is desired. Therefore, whenever the term "saccharide compound" is used in the present specification and claims, it is understood to include not only the free acid form of the conjugate but also the acetylated conjugates as well as pharmaceutically acceptable salts and esters thereof as discussed hereinabove.

The selectivity of the saccharide compounds toward tumors can be greatly increased and the possible deconjugation of the toxic aglycones in healthy parts of the body can be greatly minimized by administering to the patient, prior to or simultaneously with administration of the conjugate, an alkalinizing agent which will maintain the pH of the rest of the body at a pH of about 7.4. It is known that the activity of β-aglycosidases is substantially nil at a pH of 7.4. Thus, the administration of alkalinizing agents such as bicarbonates or other basic salts will substantially decrease and eliminate β-glycosidase activity which occurs naturally in certain healthy tissues such as the kidneys, spleen and liver. Such an administration of alkalinizing agent will not diminish the acidity of the tumor cells themselves, however, in view of the naturally low pH of the tumor cells, the mechanism of prior hyperacidification and the lack of substantial blood perfusion through the tumor area, as well as other possible mechanisms. It has been suggested in the literature, in fact, that bicarbonate will actually increase the activity of the cancer cells, cf. Gullino et al. *J.N.C.I.* 34 (6): 857–969, 1965.

Since the saccharidase activity of the tumor cells is enhanced by acidification, and the saccharidase activity of the rest of the body, particularly of the kidneys, will be substantially eliminated by alkalinization, the cytotoxic phenols will only be released at the tumor site itself due to deconjugation of the saccharides by the action the the saccharidase. Without the alkalinization step, substantial amount of toxic materials may be released, for example in the kidneys, and the cytotoxic phenols so released may cause substantial damage to these organs if there is any tyrosinase present at this site. Thus, only through the use of the present invention can saccharides of phenols which are toxic to tumor cells be used with a great degree of safety and efficacy. The greater the toxicity of the phenols after action of tyrosinase, the more important is the alkalinization step.

Other steps for increasing saccharidase activity at the tumor cells may also be undertaken. One method of accomplishing this is to elevate the temperature of the toxic cells at the time of treatment. This may be done by elevating the temperature of the entire body such as by the use of a pyrogenic drug or by elevating the temperatures solely in the are of the tumor cells, such as by microwave radiation or electrical current. Raising of the temperature increases saccharidase activity, thereby increasing the efficiency of the deconjugation of the saccharides. It is known that, in the temperature range of about 35° to 45° C., an elevation of temperature of 3° C. increase saccharidase activity by up to 50%.

Known pyrogenic drugs that can be administered to raise body temperature include etiocholanolone, progesterone, dinitrophenol, dinitrocresol, and the like. Because dinitrophenol and dinitrocresol are also cytotoxic, the use of these compounds is preferred, particularly when they are administered as the saccharide. In this case, when the saccharide is deconjugated at the tumor site, the aglycone will act not only to denature the cytoplasmic protein, but also to raise the temperature directly in the region of the tumor cells, thus greatly increasing the efficiency of further deconjugation.

Local hypothermia in the region of suspected tumor cells is preferred to general hyperthermia, because general hyperthermia will also increase the saccharidase activity in healthy cells. However, because of the alkalinization step, this is not a major problem. If the hyperthermia is local, then this provides an additional degree of certainty that the glucuronides will only become deconjugated at the tumor site. The application of microwave treatment directed at the suspected tumor site is one way to achieve total hyperthermia. Due to the different electrical resistance of tumor cells, another method of achieving some degree of local hyperthermia is by administering a low electrical current through the body.

A further manner of increasing saccharidase activity selectively at tumor cells is by administration of estrogen to female patients or testosterone to male patients, for tumors which are not estrogen- or progesterone-dependent. It has been reported that these compounds induce saccharidase activate in trophoblastic cells. Since certain tumor cells are known to be trophoblastic, this method is particularly useful for those types of cells. The alkalinization step would prevent damage to healthy trophoblastic cells.

Before treatment of patients in accordance with the present invention, it should be ascertained that the particular type of tumor involved has both a high saccharidase activity as well as a high tyrosinase activity. This may be done in a number of ways. One way is to assay tumor cells obtained in a biopsy for saccharidase activity. If such a test is positive, then the pharmaceutical compositions of the present invention may be administered. More particularly, by ascertaining the particular saccharidase activity of the tumor cells, one can select the particular saccharide conjugate or mixture of saccharide conjugates which will most effectively treat the tumor cells. By using a conjugate or conjugates which are cleaved by the saccharidases most abundant in the tumor cells, one can maximize the amount of cytotoxic phenolic compound delivered directly to the tumor site.

A second method is the administration of a saccharide whose aglycone has been labeled with a radioactive isotope. If, upon a full body scan, it is found that the radioisotope has accumulated at any specific areas of the body, then this will indicate not only the location of the tumor, but the fact that the tumor has sufficient saccharidase activity to deconjugate the saccharide. After this has been determined, the appropriate amount of the appropriate saccharide conjugate(s) of choice may be administered. If there are no tumors present, or the tumors are of the type which do not have saccharidase activity, then there will be no accumulation of radioisotope in the body as the alkalinization step of the present invention eliminates all saccharidase activity, and the isotope will be passed through the body.

Another method of diagnosing tumors which are treatable by means of the present invention, and to determine which saccharide or saccharides should be used to form the conjugates, is to test for the presence of free glucuronic acid in the urine. While the presence of glucuronides in the urine is common, the presence of free glucuronic acid in the urine, and particularly the presence of increasing amounts of glucuronic acid when tested over a period of several days, is a potent indication of the presence of tumors with β-glucuronidase activity. It has been hypothesized that the presence of free glucuronic acid in the urine in cancer patients is caused by the action of β-glucuronidase in the cancer cells on the intercellular filaments and connective tissue. Glucuronic acid is a reaction product of such activity because the intercellular filaments and connective tissues are composed of polymer of which glucuronic acid is an element, and which are known substrate for the enzyme β-glucuronidase.

A method for distinguishing free glucuronic acid from conjugated glucuronides in the urine has previously been disclosed in Rubin, U.S. Pat. No. 4,337,760. Both glucuronides and glucuronic acid give a chromogenic complex with tetraborate in concentrated sulfuric acid which reacts with m-hydroxydiphenyl to create a colored water-soluble complex. When lead acetate is added at an alkaline pH, the glucuronides precipitate and the addition of ditizone (dithiosemicarbazone) makes a stable complex with the excess lead. Accordingly, an optical reading may be taken representative of the amounts of total glucuronides and free glucuronic acid after tetraborate and m-hydroxydiphenyl have been added. A second reading may then be taken after the conjugated glucuronides and excess lead have been removed from the aqueous phase by the addition of basic lead acetate and after ditizone has been added. Alternatively, the conjugated glucuronides can be removed by reaction with barium hydroxide. The addition of barium hydroxide to the urine sample will cause precipitation of the conjugated glucuronides but not of the free glucuronic acid. After centrifugation and filtration the conjugated glucuronides are eliminated and what remains is only the free glucuronic acid. A reading representative of the amount of free glucuronic acid many then be taken. The alternative procedure bypasses the necessity of the use of ditrizone.

In the urine test for glucuronidase activity, normal patients exhibit between 200 and 400 mg per 24 hours of free glucuronic acid in the urine. Cancer patients with well developed tumors which have β-glucuronidase activity show greater than 200 to 7000 mg per 24 hours of free glucuronic acid. Accordingly, using this above test, if more than about 400 mg per 24 hours of free glucuronide is exhibited, this is an excellent indication of the presence of tumors having a high β-glucuronidase activity.

A negative indication on this urine test will not conclusively rule out the presence of tumors having β-glucuronidase activity, because tumors in their initial stages, although they might have β-glucuronidase activity, might not release sufficient free glucuronic acid to cause a positive reading of the urine. Therefore, the urine test should be repeated, and if an increasing amount of free glucuronic acid is found, then this is another indication of the presence of a tumor having β-glucuronidase activity.

Although 4-hydroxyanisole and other cytotoxic phenols may not generally be toxic to healthy cells, when these substances are substrates to tyrosinase, they are converted to toxic metabolite which have their dominant effect inside the cells, where they are produced (i.e., melanoma cells and melanocytes), as tyrosinase is known to convert several phenols (e.g., its natural substrate, tyrosine) to catechols and quinones which react strongly with SH groups.

Tyrosinase activity of tumor cells can be determined by assaying a sample obtained from a biopsy by the method of Pomerantz, $J. Biol. Chem.$ 241: 161, 1966, using L-[3,5-$^3$H] -tyrosine (Amersham TRK 200). Using this method, Wallevik et al. (op. cit.) determined that melanotic melanoma had the greatest tyrosinase activity, while bladder carcinoma and amelanotic melanoma had less but measurable tyrosinase activity. Skin fibroblasts were found to have no tyrosinase activity.

Once it has been determined that the patient has a tumor having both tyrosinase and saccharidase activity, the first step of the treatment is to administer a dose of glucose, such as 100 grams of honey, glucose, or other simple sugar. Before treatment with the conjugates, an intravenous drip is administered of a solution in distilled water containing approximately 10% glucose and 60-millequivalents sodium bicarbonate. Approximately one liter of this solution is administered, assuming no contraindications, and the pH of the urine is checked to determine that it has reached a pH of approximately 7.4. This establishes that the system has become alkalinized and it is now safe to administer the glucuronide. Another liter of the same glucose-bicarbonate solution containing the desired amount of conjugate of conjugates is then administered. This administration is repeated daily as needed. It is desirable to maintain high levels of glucose in the blood during treatment according to the present invention, unless the saccharide is glucose, of course. When glucose levels in the blood are increased, they are generally increased at least 180%, and preferably above 250% of normal.

When galactose is the saccharide of choice, exogenous galactose should not be administered to the patient, such as from dairy products. In the same manner, when another saccharide conjugate is administered, the patient should not receive exogenous saccharide so that the saccharidase activity can be centered on the conjugate, and not on exogenous saccharide.

If there are contraindications for the administration of bicarbonate parenterally, then an antacid may be orally administered. This antacid may be any conventional antacid such as sodium bicarbonate, magnesium bicarbonate, aluminum hydroxide, aluminum magnesium silicate, magnesium carbonate, magnesium hydroxide, magnesium oxide, or the like. The important criterion is that the pH of the urine become approximately 7.4 and remain so during treatment.

The hyperacidification of the tumor cells is caused by a hyperglycemic condition in the patient. Therefore, any hyperglycemic agent may be used as the hyperacidification agent, as, for example, fructose, galactose, lactose or glucagon. Furthermore, it should be understood that this hyperglycemic condition may be effected in any known manner. For example, if the patient is diabetic, then the condition can be brought about by decreasing the insulin administration. Of course, the hyperacidification agent should not be the same saccharide as the conjugate to be administered.

Any agent which will raise the pH of the urine to approximately 7.4 can be used as the alkalinizing agent, including sodium or potassium bicarbonate or citrate, or other basic salts or antacids. While it is preferred that these agents be administered intravenously, they may be administered orally.

When the term "approximately 7.4" is used in the present specification and claims, with respect to the pH level to be maintained in the rest of the body, it should be understood that a pH level slightly above or below 7.4 may be used, although this is not preferred. Of course, this pH does not apply to the gastrointestinal tract, where the pH may vary substantially from about 7. As the pH deceases from 7.4, the β-glucuronidase activity increases until the optimal pH is reached. Furthermore, below pH 7.0 the rest of the body will not be alkaline but will be acid. Above 7.4 the danger of alkalosis increases without any substantial further decrease in β-glucuronidase activity. A pH level of 7.4 is preferred, as this is physiological pH and cannot be harmful to the body, and it is known that the β-glucuronidase activity in healthy organs is substantially nil at this pH level.

As indicated above, the lactose or glycoconjugate thereof can be administered enterally as well as parenterally. Both lactose and the glycoconjugates are metabolized and excreted from the body in a known manner. However, since lactose is digested by lactase present in the gastrointestinal tract to galactose and glucose, the lactose should not be administered orally.

By creating a relatively high serum level of lactose, the crucial stages of the organ cell lectins can be blocked as long as there is a danger of an increased metastasization, e.g., due to treatment of the primary tumor. This should also be effected before and during surgical interventions, during which time tumor cells may readily be released into the blood.

The dosage of the compounds administered should be monitored to avoid any side effects due to the massive release of toxins caused by the dying cancer cells. It may be preferable to treat the patient with the compounds of the present invention in short courses of several days, leaving several days in between to allow any toxins released by the dying cancer cells to leave the body before continuing with treatment.

Upon administration to patients of about 50 to 300 g of lactose per day in case of a diagnosed colon carcinoma from the time of diagnosis until four weeks after successful therapy for the colon carcinoma, no liver metastases were observed, although these metastases are statistically very frequently observed in patients affected with colon cancer. These amounts of lactose are well tolerated over an extended period of time without the occurrence of side effects.

When the lactose is administered to patients to prevent metastases resulting from surgery or diagnostic intervention, the administration of lactose begins preferably about 8–12 hours before surgery or diagnostic intervention and is generally continued three days post-operatively. Longer administration can be carried out in the absence of side effects. Lactose is administered so as to supply a total dosage of about 0.5 to about 6 mg/kg of body weight in 24 hours by infusion every eight hours.

To prevent cancers is persons who are in danger of contracting cancer, lactose is administered prophylactically. Lactose can be administered parenterally two or three times per month in approximately the same dosages used to prevent metastasis, i.e., to provide sufficient lactose to provide a serum in a patient of about 0.5 to 5 mM lactose. This is of particular importance for persons with a family history of cancer, who have a genetic predisposition for cancer, or for those who have been exposed to known carcinogens, such as cigarette smoke or asbestos.

Of particular interest is a conjugate of lactose with PMP and benzoic acid. When this conjugate reaches the site of a tumor, the benzoic acid is oxidized to benzaldehyde, which is extremely toxic to the receptor sites on a tumor. Once the benzaldehyde has destroyed the receptor sites on the tumor by crosslinking these receptors, there is little danger of metastasis from the tumor, and therapy can then be concentrated solely on destroying the tumor.

Another compound of particular interest is a conjugate of 7-hydroxy coumarin with lactose. This compound, which is extremely toxic when administered by itself, is safely administered as a conjugate with lactose or another saccharide, particularly in the treatment of prostate and lung cancer. The conjugation of 7-hydroxy coumarin with a saccharide enables sufficient amounts of the 7-hydroxy coumarin to be delivered to the tumor site to destroy the tumor without destroying normal cells in the body.

When a lactose conjugate with a cytotoxic agent is administered, it must not be administered orally. Intramuscularly is a preferred method of administration, with the lactose dissolved in a suitable carrier, e.g., water. When the lactose is administered as part of a conjugate, the amount to be administered depends upon the particular cytotoxic drugs used. However, one skilled in the art can readily determine the optimum amount of the conjugate to be administered, taking into account the patient's condition, the size of the tumor, etc. For example, using New Drug Exemption Guidelines published by governmental authorities, one skilled in the art can readily establish preclinical and clinical trials for determining the preferred dos;ages to be used. One skilled in the art would, by use of methods described in standard textbooks, guidelines and regulations as described above, as well as common general knowledge within the field, be able to select the exact dosage regiment to be implemented for any selected conjugate using merely routine experimentation procedures.

In determining dosages of the conjugates to be administered, the dosage and frequency of administration is selected in relation to the pharmacological properties of the specific conjugate. Normally at least three dosage levels should be used. In toxicity studies in general the highest dose should reach a toxic level but be sublethal for most animals in the group. If possible, the lowest dose should induce a biologically demonstrable effect. These studies should be performed in parallel for each conjugate selected.

Additionally, the IC50 level of the conjugate in question can be one of the dosage levels selected and the other two selected to be higher and/or lower. If the highest dose does not reach a toxic level, and the lowest does does not indicate a biologically demonstrable effect, e.g., destruction of the tumor, the toxicology tests should be repeated using appropriate new doses calculated on the basis of the results obtained. Young, healthy mice or rats belonging to a well-defined strain are the first choice of species, and the first studies use the intramuscular, the preferred, route of administration. Control groups given a placebo or being untreated are included in the tests. Test for general toxicity as outline above should normally be repeated in another non-rodent species, e.g., a rabbit or dog.

Studies may also be repeated using other routes of administration, bearing in mind that the lactose conjugates should not be administered orally.

Further single dose toxicity tests should be conducted in such a way that signs of acute toxicity are revealed and the mode of death determined. The dosage to be administered is calculated on the basis of the results obtained in the above mentioned toxicity tests. It may be desired not to continue studying all of the initially selected conjugates. Data on single dose toxicity, e.g., LD50, (the dosage at which half of the experimental animals die) is to be expressed in units of or weight or volume per kg of body weight and should generally be furnished for at least two species with different modes of administration. In addition to the LD50 value in rodents, it is desirable to determine the highest tolerated dose and/or lowest lethal dose for other specious, e.g., dog and rabbit.

When a suitable and presumably safe dosage level has been established as outlined above, studies on the drug's chronic toxicity, its effect on reproduction and potential mutagenicity may also be required in order to ensure that the calculated appropriate dosage range will be safe, also with regard to these hazards.

Pharmacological animal studies on pharmacokinetics revealing, e.g., absorption, distribution, biotransformation and excretion of the conjugate and metabolites are then to be performed. Using the results obtained, studies on human pharmacology are then designed. Studies of the pharmacodynamics and pharmacokinetics of the conjugate in humans should be performed in healthy subjected using the routes of administration intended for clinical use, and can be repeated in patients. Dose-response relationship when different doses are given should be studied in order to elucidate the dose-response relationship (dose vs. plasma concentration vs. effect), the therapeutic range and the optimum dose interval. Also, studies on time-effect relationship, e.g., studies into the time-course of the effect and studies on different organs in order to elucidate the desired and undesired pharmacological effects of the drug in particular on other vital organ systems should be performed.

The conjugate is then ready for clinical trials to compare the efficacy of the conjugate to existing therapy. A dose-response relationship for therapeutic effect and for side effects can be more finely established here.

Besides intravenous administration, the acid form of the glucuronide conjugates may be administered by any means of parenteral administration. However, the free acid form of the glucuronides should not be administered orally, as it is known that $\beta$-glucuronidase is present in the digestive tract. The tri-acetylated conjugates, however, can be administered orally, as the $\beta$-glucuronidase in the digestive tract does not affect the acetylated conjugates.

The amount of conjugate to be administered to any given patient must be determined empirically and will differ depending upon the condition of the patient. Relatively small amounts of the conjugates can be administered at first, with steadily increasing dosages if no adverse effects are noted. Of course, the maximum safe toxicity dosage as determined in routine animal toxicity tests should ever be exceeded.

Optimally, the concentration of conjugates to be administered may be sufficient to provide a concentration of approximately 0.5 to about 5 mM of lactose, either alone or combined with sufficient conjugate to provide from about $5 \times 10^{-4}$M to about $5 \times 10^{-3}$M of the phenolic cytotoxic compound to the tumor site.

It is clear that any tumor cells having both tyrosinase activity and saccharidase activity may be treatable in accordance with the present invention, with the remaining organs of the body being protected by the alkalinization step. Tumors which are known to have saccharidase activity include solid breast tumors and their metastases, bronchogenic carcinoma and its metastases, and lymphomas, as well as lung carcinoma, colon carcinoma, testicular carcinoma, hepatic carcinoma, pancreatic carcinoma, ovarian carcinoma, leukemia, bronchogenic carcinoma, prostate carcinoma, Hodgkin's disease and rectal carcinoma. Tumors which have high tyrosinase activity, as noted above, include melanoma, amelanotic melanoma, and breast carcinoma, and bladder carcinoma, as well as a number of other noted above.

Of course, the combination of conjugates must be chosen so that the saccharides compete for the same receptor on the membrane of the cancer cells. Since, for example two glucuronides cannot be used together, one can use a glucuronide conjugate with a galactose conjugate if the tumor has both $\beta$-glucosidase activity and $\beta$-galactosidase activity. As noted above, one skilled in the art can readily determine which type of activity a tumor has without undue experimentation.

It is also known that neoplasms which do not have high saccharidase activity, and therefore cannot be treated in accordance with the present invention, include some leukemias. It must be understood, however, that these lists are not exhaustive, and that the art is aware of many other types of tumors which have saccharidase activity. Moreover, one skilled in the art can readily determine which type of saccharidase activity a tumor has by using the techniques described above. If it is determined that the tumor does indeed have both saccharidase activity and tyrosinase activity, the therapeutic treatment of the present invention can be effectively used.

When it is desired to induce hyperthermia to increase saccharidase activity, a method should be selected by which the temperature is raised as much as possible without risking damage to healthy portions of the body, such as the eyes. An increase of about 2° C. for whole body hyperthermia, and as much as 4.5° C. for local hyperthermia, is preferred. The hyperthermia should be timed to last about an hour at the time of greatest saccharide concentration at the tumor site. For example, when local microwave treatment is selected, it should begin about one half hour after commencement of the intravenous conjugate drip and be continued for about one hour. The proper dosage of known pyrogens to achieve the desired degree of hyperthermia would be known to those skilled in the art, and can be easily empirically determined without undue experimentation. A dosage of about 30 ng/day of dinitrophenol, for example, would be appropriate.

Because the triacetylated form of the conjugate is not affected by saccharidase in the digestive tract, this form of the conjugate can be administered orally without loss of activity. Moreover, it has been found that, because the triacetylated form of the conjugate is lipid soluble, it is retained in the body for a much longer time than the free acid form of the conjugate. The tri-acetylated form of the conjugate provides an additional level of protection of normal cells, as the phenol compound is not released in the body until the acetyl groups are removed and the saccharide is removed from the phenolic compound. Since primitive cells produce acetylase, this acetylase removes the acetyl groups from the conjugate. The more anaplastic (more immature) the tumor cells, the more enzymes it produces, so that the triacetylated form of the drug is more selectively toxic tumor cells than even the conjugated form. Thus, since two steps are required to liberate the phenolic compound, the conjugates are even more preferentially delivered to the site of an active tumor than are the acid form of the conjugates.

When estrogen or testosterone are administered, a dosage of from about 3-15 mg/kg body weight/day provides the desired inducement to saccharidase activity.

To treat a patient suffering from cancers which exhibit tyrosinase activity as well as saccharidase activity, the phenolic compounds are administered in the form of saccharide conjugates or acetylated saccharide conjugates. When administered in the form of saccharide conjugates per se, the conjugates must be administered parenterally. However, when administered as the acetylated conjugates, the conjugates can be administered orally, most conveniently as capsules.

Capsules are formulated, generally containing approximately 0.6 gram/capsule of active ingredient. When only one conjugate is administered, the dosage is generally about five to about ten capsules three times daily, providing nine to about twenty grams per day of active ingredient (conjugate). The patient's serum is measured after a loading dosage of the compound is administered to maintain a level of approximately 1 mM of the compound in the serum.

When a combination of conjugates is administered, however, the number of capsules of each conjugate can be greatly decreased. For example, when a combination of a glucuronide and a galactoside are administered as conjugates, rather than five to ten capsules daily, only from about 2 to five capsules, containing approximately 0.6 gram per capsule of combined active ingredients, need be administered three times daily. The amount of active ingredients in the serum need only be maintained at approximately 0.25 to about 0.5 mM of combined active ingredients.

As noted above, para-methoxy-phenyl glucuronide is the preferred compound for use according to the present invention, either alone or in combination with another saccharide conjugate, particularly lactose, of para-methoxy-phenol. This compound is preferred because it is particularly non-toxic to the non-cancerous cells, and because when lactose is the saccharide in the conjugate the lactose is delivered with the cytotoxic compound. As with other saccharide compounds of the present invention, the para-methoxy-phenyl glucuronide can be used in either the tri-acetylated form or in the free acid form.

In the first step after administering para-methoxy-phenyl saccharide to a patient, the "prodrug" is hydrolyzed at the cancer site by the saccharidase to yield 4-hydroxy anisole. This reaction takes place only at the cancer site because only at the cancer site is the saccharidase enzyme available to catalyze the reaction. The 4-hydroxy anisole that is released is then available as a substrate for the second reaction, which is catalyzed by the enzyme tyrosinase. The tyrosinase oxidizes the 4-hydroxy anisole to methoxy-ortho-benzoquinone. The methoxy-ortho-benzoquinone is an unstable molecule that spontaneously releases hydrogen peroxide. When the hydrogen peroxide reaches a certain concentration, living membranes can no longer cope with the oxidative damage produced thereby, and are destroyed. To enhance the oxidative damage in these cancerous cells, the hydrogen peroxide concentration is further increased by inhibiting the reducing enzyme glutathione reductase.

The para-methoxy saccharide is particularly important because this particular type of prodrug becomes extremely toxic after two sequential steps of activation and potentiation, and concomitant inhibition of a third enzyme, glutathione reductase. This occurs via two sequential enzymatic systems that exist only at the malignant growth, i.e., saccharidase and tyrosinase.

By using any specific inhibitor of glutathione reductase, it was possible to increase the damage inflicted on the cancerous cells by para-methoxy-phenyl saccharide. The most promising, least toxic inhibitors of glutathione reductase are based upon the anti-malaria drug chloroquine. Of these compounds, chloroquine diphosphate is particularly useful. However, other compounds that can inhibit glutathione reductase include quinine or quinidine, quinine acetylsalicylate, quinine benzoate, quinine bisalicyloylsalicylate, quinine bisulfate, quinine carbonate, quinine dihydroiodide, quinine dihydroboride, quinine dihydrochloride, quinine ethylcarbonate, quinine ethyl sulfate, quinine formate, quinine gluconate, quinine glycerophosphate, quinine hydroiodide, quinine hydrobromide, quinine hydrochloride, quinine hypophosphate, quinine lactate, quinine phenolsulfonate, quinine salicylate, quinine sulfate, quinine tannate, and quinine urea hydrochloride.

Other inhibitors of glutathione reductase that can be used include metronidazole, methimazole, iodo-acetamide, BiCNCl, and cormastine, which latter compound is an anti-cancer drug itself. Nifulidone, which is an antibiotic, and its derivatives, can also be used to inhibit the activity of glutathione reductase.

Because para-methoxy-phenylsaccharide is a saccharide, it is hydrolyzed by the saccharidase produced by tumor cells to release 4-hydroxy anisole at the site of the tumor. The pH for optimal enzymatic activity for most saccharides is about 5.5, so that acidification of the tumor is desirable. This acidification of the tumor, as described elsewhere in this specification, can be achieved by administering glucose to the patient thirty minutes prior to the treatment, as orally administered glucose expressed itself in acidification of the tumor due to accumulation of lactic acid. Of course, if the prodrug used is a glucose conjugate, an acidification compound other than glucose is administered.

In a preferred treatment protocol, the patient is preferably on maintenance dosage of a corticosteroid, such as 4 mg of dexamethasone, throughout the duration of the treatment. This dosage ensures delay in premature fibrotic changes and interference with the blood and drug supply to the tumor. Of course, any of the conventional corticosteroids can be used for this purpose.

It should also be noted that corticosteroids inhibit the production of tumor necrosis factor, and thus reduce the malaise, loss of appetite, and cachexia that accompany malignant diseases. In addition, corticosteroids help in maintaining high levels of blood glucose, and for brain tumors, a higher dosage is useful. Omeprazole, Zantac, Cimetidine or other anti-ulcer drugs should also be administered concomitantly to prevent ulcers, since corticosteroids are know to induce ulcers.

During therapy according to the present invention, no vitamin C supplementation or any ascorbate should be administered to the patient. Ascorbates, being antioxidants, protect the malignant cells from the oxidative damage caused by the metabolites of the cytotoxic phenolic compounds. Any vitamin E administered acts as an antioxidant, and reduces the tyrosinase.

Additionally, during therapy no compounds should be administered which are substrates for the enzyme of the tumor sought to be used for acting on the conjugate administered. For example, if the conjugate used is one with galactose, the patient should avoid galactose-containing foods. Likewise, where glucose is the conjugate, glucose-containing foods should be avoided.

The conjugates of the present invention to be used in conjunction with lactose administration can be administered singly or in combination to patients suffering from tyrosinase-dependent cancers at doses ranging from about 0.5–15 grams/day of total dosage. Although it has been found that maintaining a serum level of about 0.5 to 1 mM of conjugate is desirable, serum levels ranging from about 0.05 mM to about 10 mM can be used, depending upon the patients' response to the treatment. As noted above, one skilled in the art can readily ascertain what saccharide or saccharides should be used to prepared conjugates to treat a particular tumor, and can tailor the prodrugs accordingly. As noted above, synergistic effects are obtained by combining conjugates. Some of these synergistic combinations include conjugates of β-glucuronides with galactosides for treating mammary tumors, and α-glycosides with β-glucuronides for treating melanomas. Determination of preferred combinations for each tumor type is well within the skill of the art.

The lactose or lactose conjugate can be incorporated in any conventional solid or liquid pharmaceutical formulation n any concentration desired. For example, injectable compositions, compositions which may be adsorbed through the mucosa, or transdermally administrable solutions may be used. The pharmaceutical formulations of the invention comprise an effective amount of lactose or of the lactose conjugate, its analogue, or other compound causing the release of lactose.

In addition to the pharmacologically active conjugates or lactose alone, the new pharmaceutical preparations may contain suitable pharmaceutically acceptable carriers comprising excipients and auxiliaries which facilitate processing of the conjugates into preparations which can be used pharmaceutically. These compositions, such as suppositories for rectal administration, as well as suitable solutions for administration by injection or by parenteral administration, contain from about 0.01 to 99 percent, preferably from about 20 to 75 percent, of active compound, together with the excipient.

Pharmaceutical preparations which can be used rectally include, for example, suppositories which consists of a combination of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of lactose or of a combination of lactose and a water-soluble form of the conjugate. In addition, suspensions of the active compounds as appropriate oily injection suspensions may also be administered. Suitable lipophilic solvents or vehicles include fatty oils, such as sesame oil, or synthetic fatty acid esters, such as ethyl oleate or triglycerides. Aqueous injection suspension that may contain substances which increase the viscosity of the suspension include sodium carboxymethyl cellulose, sorbitol, and/or dextran.

Administration may be by parenteral, subcutaneous, intravenous, intramuscular, intraperitoneal, or transdermal routes. As noted above, the dosage administered will be dependent upon the age, health, and weight of the recipient, type of concurrent treatment, if any, frequency of treatment, and the nature of the effect desired.

Each formulation according to the present invention may additionally comprise inert constituents including pharmaceutically acceptable carriers, diluents, fillers, salts, and other materials well known to the art, the selection of which depends on the dosage form used, the particular purpose to be achieved according to the determination of the ordinarily skilled artisan in the field, and the properties of such additives. Examples of carriers and diluents include carbohydrates, lipids and water.

The conjugates of the present invention can be combined with a pharmaceutically acceptable carrier therefore, and optionally other therapeutic and/or prophylactic ingredients. The carriers must be "acceptable" in the sense of being compatible with the other ingredient of the formulation, and not deleterious to the recipient thereof.

Pharmaceutical formulations suitable for oral administration of the conjugates wherein the carrier is a solid are most preferably presented as unit dose formulations such as boluses, capsules, and the like, as well as sachets or tables, each containing a predetermined amount of active ingredient. A tablet may be made by compression or molding, optionally with one or more accessory ingredients. Compressed tablets may be prepared by compressing in a suitable machine the active conjugate of mixture of active conjugates in a free-flowing form, such as a powder or granules, optionally mixed with a binder, lubricant, interdiluent, lubricating, surface active or dispersing agent. Molded tablets may be made by molding the active conjugate with an inert liquid diluent. Tablets may be optionally coated and, if uncoated, may optionally be scored. Capsules may be prepared by filling the active conjugate, either alone or in admixture with another conjugate and.or with one or more accessory ingredients, into the capsule cases and then sealing them in the usual manner. Sachets are analogous to capsules, wherein the active conjugate or conjugates, together with any optional accessory ingredients, are sealed in a rice paper envelope.

Pharmaceutical formulations suitable for oral administration of the conjugates in which the carrier is a liquid may conveniently be presented as a solution in a pharmaceutically acceptable solvent which is inert to the conjugates included therein.

Pharmaceutical formulations suitable for parenteral administration are conveniently presented in unit dose or multi-dose containers which are sealed after introduction of the formulation unit required for use.

It should be understood that in addition to the aforementioned carrier ingredients, the pharmaceutical formulations described above may include, as appropriate, one or more additional carrier ingredients such as diluents, buffers, lubricants, preservatives and the like, and substances included for the purpose of rendering the formulation isotonic with the blood of the intended recipient.

The pharmaceutical formulations may be any formulations in which the active compound or compounds may be administered, and include those suitable for oral or parenteral (including intramuscular and intravenous) administration. The formulations may, where appropriate, be conveniently presented in discrete dosage units and may be prepared by any of the methods woo known in the art of pharmacy. All of the methods include the step of bringing into association the active compound with liquid carriers of finely divided solid carrier, or both, and then, if necessary, shaping the product into the desired formulation.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein or for the purpose of description and not of limitation.

What is claimed is:

1. A method for inhibiting metastases of malignant tumor cells or metastases of malignant cells associated with Hodgkin's disease comprising administering to a patient afflicted with such a malignant tumor or with Hodgkin's disease an effective amount of at least one conjugate made by conjugating a saccharide or a pharmaceutically acceptable ester or salt thereof to a cytotoxic phenolic compound which is a substrate for tyrosinase.

2. The method according to claim 1 wherein the conjugate is formed from the triacetylated form or the heptacetylated form of the saccharide.

3. The method according to claim 2 wherein the at least one conjugate is administered orally.

4. The method according to claim 1 wherein the cytotoxic phenolic compound is selected from the group consisting of 4-hydroxyanisole, L-3,4-dihydroxyphenylalanine, dopamine, tert-butylcatechol, hydroquinone, 6-hydroxydopa, 4-tert-butyl phenol, 7-hydroxy coumarin, 4-tert-amyl phenol, 4-benzomethoxy phenol and methyl gallate.

5. The method according to claim 4 wherein the cytotoxic compound is 4-hydroxyanisole.

6. The method according to claim 1 wherein the saccharide is selected from the group consisting of glucuronides, glucose, galactose, fructose, arabinose, mannose, gulose, ribose, xylose, lyxose, erythrose, maltose, cellobiose, lactose, sucrose, N-acetylglucosamine, N-acetylgalactosamine, rhamnose and mixtures thereof.

7. The method according to claim 1 further comprising administering to said patient an effective amount of a compound that inhibits the activity of glutathione reductase.

8. The method according to claim 7 wherein said compound that inhibits the activity of glutathione reductase is selected from the group consisting of chloroquine diphosphate, quinine, quinidine, quinine acetylsalicylate, quinine benzoate, quinine bisalicyloylsalicylate, quinine bisulfate, quinine carbonate, quinine dihydroiodide, quinine dihydrobromide, quinine dihydrochloride, quinine ethylcarbonate, quinine ethyl sulfate, quinine formate, quinine gluconate, quinine glycerophosphate, quinine hydroiodide, quinine hydrobromide, quinine lactate, quinine phenolsulfonate, quinine salicylate, quinine sulfate, quinine tannate, iodo-acetamide, metronitrazole, methionazole, nifulidone, derivatives of nifulidone, carnitine, and quinine urea hydrochloride.

9. The method according to claim 8 further comprising administering to said patient an effective amount of a corticosteroid to maintain high levels of glucose in the blood above about 180% of normal glucose levels in the blood.

10. The method according to claim 1 wherein the cytotoxic compound is selected from the group consisting of 7-hydroxycoumarin, benzoic acid, 4-hydroxyanisole, L-3,4-dihydroxyphenylalanine, dopamine, tert-butylcatechol, hydroquinone, 6-hydroxydopa, and methyl gallate.

11. The method according to claim 10 wherein the cytotoxic compound is 4-hydroxyanisole.

12. The method according to claim 10 wherein the cytotoxic compound is benzoic acid.

13. A composition for inhibiting metastasis of a malignant tumor and for selectively treating tumor cells which have both saccharidase activity and tyrosinase activity comprising an effective amount of lactose and a conjugate made by conjugating at least one saccharide compound selected from the group consisting of saccharides and pharmaceutically acceptable esters and salts thereof to a cytotoxic phenolic compound which is also a substrate for tyrosinase, and a pharmaceutically acceptable carrier.

14. The composition according to claim 13 wherein said saccharide compound is selected from the group consisting of glucuronides, glucose, galactose, fructose, arabinose, mannose, gulose, ribose, xylose, lyxose, erythrose, maltose, cellobiose, lactose, sucrose, N-acetylglucosamine, N-acetylgalactosamine, rhamnose and mixtures thereof.

15. The composition according to claim 13 wherein the saccharide compound is a triacetylated or a heptacetylated saccharide.

16. The composition according to claim 13 wherein the cytotoxic phenolic compound is selected from the group consisting of benzoic acid, 4-hydroxyanisole, tyrosine, L-3, 4-dihydroxyphenylalanine, dopamine, tert-butylcatechol, hydroquinone, 6-hydroxydopa, and methyl gallate.

17. The composition according to claim 16 wherein the cytotoxic compound is 4-hydroxyanisole.

18. The composition according to claim 16 wherein the cytotoxic compound is benzoic acid.

19. The composition according to claim 16 wherein the cytotoxic compound is 7-hydroxycoumarin.

20. The method according to claim 1 wherein the tumor cells are selected from the group consisting of solid breast tumors, lung carcinoma, colon carcinoma, testicular carcinoma, hepatic carcinoma, pancreatic carcinoma, ovarian carcinoma, bronchogenic carcinoma, prostate carcinoma, and rectal carcinoma.

21. The method according to claim 20 wherein the tumor cells are solid breast tumors.

22. The method according to claim 1 wherein the conjugate is para-methoxy-phenyl lactose.

23. Para-methoxy-phenyl lactose.

* * * * *